United States Patent [19]
Edwards et al.

[11] Patent Number: 5,464,097
[45] Date of Patent: * Nov. 7, 1995

[54] SHOCK PROTECTION PACKAGING FOR LIQUIDS

[75] Inventors: David B. Edwards; William J. McCarthy; Alan J. Aldred, all of Dagenham; Anthony D. Jackman, Pyrford, all of United Kingdom

[73] Assignee: May & Baker Limited, Dagenham, United Kingdom

[*] Notice: The portion of the term of this patent subsequent to Mar. 7, 2012, has been disclaimed.

[21] Appl. No.: 372,553

[22] Filed: Jan. 13, 1995

Related U.S. Application Data

[63] Continuation of Ser. No. 179,878, Jan. 11, 1994, Pat. No. 5,394,990, which is a continuation of Ser. No. 920,026, Jul. 27, 1992, abandoned, which is a continuation of Ser. No. 825,417, Jan. 24, 1992, abandoned, which is a continuation of Ser. No. 623,997, Feb. 14, 1991, abandoned.

[30] Foreign Application Priority Data

Jun. 15, 1988 [GB] United Kingdom ............... 8814158
Jun. 15, 1988 [GB] United Kingdom ............... 8814159
Feb. 17, 1989 [GB] United Kingdom ............... 8903707

[51] Int. Cl.⁶ .......................... B65D 85/82; B65D 81/02
[52] U.S. Cl. .................. 206/524.7; 206/0.5; 206/521; 220/359; 220/403
[58] Field of Search ................. 239/53, 55, 57, 239/34; 43/125, 129, 131, 132.1; 206/0.5, 521, 524.7, 592, 594; 220/403, 404, 409, 413, 420, 425, 462, 359

[56] References Cited

U.S. PATENT DOCUMENTS

| | | | |
|---|---|---|---|
| 1,801,921 | 4/1931 | Hollis | 206/221 |
| 2,766,067 | 10/1956 | Shinberg | 239/55 X |
| 3,321,070 | 5/1967 | Childs | 220/403 X |
| 3,355,080 | 11/1967 | Ransing et al. | 220/404 |
| 3,534,851 | 10/1970 | Peterson et al. | 206/0.5 |
| 3,695,989 | 10/1972 | Albert | 206/524.7 X |
| 3,717,274 | 2/1973 | Wingardh | 215/1 C |
| 3,784,005 | 1/1974 | McVay | 206/219 X |
| 3,902,596 | 9/1975 | McVay | 206/219 X |
| 4,296,859 | 10/1981 | McClinton | 206/219 |
| 4,725,465 | 2/1988 | Lastovich | 206/524.7 X |
| 5,394,990 | 3/1995 | Edwards et al. | 206/524.7 |

FOREIGN PATENT DOCUMENTS

| | | | |
|---|---|---|---|
| 1376764 | 9/1963 | France. | |
| 2044386 | 2/1971 | France. | |
| 922317 | 3/1963 | United Kingdom | 206/524.7 |
| 1524037 | 9/1978 | United Kingdom. | |

*Primary Examiner*—Bryon P. Gehman
*Attorney, Agent, or Firm*—Morgan & Finnegan

[57] ABSTRACT

A package for liquid concentrates comprises an outer container (1) and an inner water-soluble or water-dispersible envelope (3) containing the concentrate. The container (1) has a shock absorbing base formed by joining a base-part (9) to the main body-part (8) with an S-shaped or corrugated strip (10), thus providing a flexible connection allowing relative movement between the base-part (9) and main body-part (8). The container (1) is sealed with a removable foil lid (2) and is tapered towards its bottom and has a wide neck to allow easy exit of the envelope (3).

32 Claims, 1 Drawing Sheet

SHOCK PROTECTION PACKAGING FOR LIQUIDS

This is a continuation of application Ser. No. 08/179,878 filed Jan. 11, 1994 now U.S. Pat. No. 5,394,190, which is a continuation of U.S. Ser. No. 07/920,026 filed on Jul. 27, 1992, now abandoned which is a continuation of Ser. No. 07/825,417 filed Jan. 24, 1992, now abandoned which is a continuation of Ser. No. 07/623,997 filed Feb. 14, 1991, now abandoned.

This Invention relates to a package for a liquid chemical or a chemical dissolved or dispersed in an organic liquid, the package being adapted to release its contents on contact with water.

Chemicals such as pesticides and herbicides and other potentially harmful materials are often produced as a concentrated solution or dispersion in an organic liquid. Such chemicals are typically supplied in a metal or blow-moulded plastics container with a screw closure. To use the chemical pesticides or herbicides a quantity of the concentrated material is measured out of the container and then mixed with a large volume of water before being sprayed onto a locus to be treated or onto plants. Such concentrated chemical solutions are usually highly toxic so great care must be taken in measuring and mixing them to avoid splashing the liquid chemical and to avoid human or animal contact with the concentrated solution or dispersion.

Efforts have been devoted to the design of containers to minimise the risk of accidental spillage or splashing when their contents are used and also to reduce liquid residues remaining in the containers after use. Plastics containers with wide necks to facilitate pouring of their liquid contents have been used. Blow moulded plastics containers having hollow handles have been made in which the hollow handles are isolated from the body of the container to avoid retention of liquid in the handle.

Nevertheless, with present packages it is relatively easy to spill the contents during the mixing process with the resulting risk of contamination of the environment and risk of contact with humans and animals. Also, it is rare to empty the container and farmers, and other users, tend to have partly full containers left around. These represent a further hazard. Even when all of the contents have been used it is difficult to dispose of the empty container. It is also difficult to wash adequately the containers and measuring instruments in which the concentrated solutions or dispersions are handled. These devices represent a further hazard to personnel and to the environment.

The present invention provides a package for a liquid comprising an outer container having a shock-absorbing base and an inner water-soluble or water-dispersible envelope containing the liquid.

The inner envelope may be disposed in the container with a space between them into which the envelope can deform under stress. The shock absorbing base may be formed by a flexible strip or corrugation in the lower part of the container joining the main part of the container to the base. This may also form an internal smooth shoulder in the container on which the envelope is supported and under which is formed the space. The container, or part of it, e.g. the foot, may be translucent to allow the user to see if leakage of the envelope has occurred. The container may be made from a semi- or substantially rigid material such as polypropylene and is preferably provided with a removable closure or lid which may comprise a flexible foil lid heat-sealed or glued to the container. The lid may be PET, PVDC, PVA, PP or Nylon laminated with aluminium and paper: PET is preferred. The lid is preferably sealed to the top of the container to provide a good barrier to leakage if the envelope breaks; it is preferably bigger than the top of the container to provide a flap which can be gripped easily to remove the lid.

A laminated lid is preferred, for example a paper/aluminium/plastics laminate in which the plastics layer can be heat sealed to the lid to provide a hermetic seal. The aluminium layer provides a barrier against any pinholes which may occur in the plastics layer. The paper provides strength, processability and a label can be printed or stuck onto it. The plastics material is preferably polyethylene terephthalate (PET) which provides a good barrier against possible leakage, has good heat sealing characteristics, allows for easy removal of the lid prior to use, does not contain halogen which is potentially damaging to the environment when the lid is to be disposed of, and withstands shock.

The container may be wide-necked and have a smooth interior to allow easy exit of the envelope and may taper towards the base to allow nested stacking of empty containers and also to provide some support against downward movement of the envelope.

The ratio of length to thickness of the flexible section may be between 7:1 and 11:1, preferably 9:1 for a polypropylene container of about 1 mm wall thickness. The flexible section may have, in cross-section a lazy S-shape so that it always slopes downwardly inwardly of the container. The package may contain a predetermined quantity of a chemical, e.g. half liter, one liter, which is a liquid or which is dissolved or dispersed in an organic liquid contained in the envelope which will release its contents on contact with water. Thus, in this case, the envelope wall would comprise a water soluble or dispersible material which is insoluble in the organic liquid.

It will be understood that liquid or solid chemicals can be dispersed in the organic liquid: the dispersion can be, for example, an emulsion or a suspension.

The envelope containing the chemical is preferably only partly full so that the envelope comprises an air space which generally occupies from 2 to 40% preferably from 4% to 10%, of the volume of the envelope. A larger space could be used but is less likely to be commercially attractive. Partial filling of the envelope reduces the risk of rupture of the envelope if it is subjected to shock and reduces the risk of rupture or leakage in the event of an increase in temperature which might make the bag swell or sweat.

The volume of chemical is preferably from a half liter to two liters: a half liter is especially preferred.

The container may have a circular cross-section but preferably, it has a substantially square or rectangular cross-section with rounded corners or sides. With such an arrangement less space is wasted when the packages are themselves packed together. The cross sectional shape of the foot portion may be similar to that of the rest of the container or, alternatively, it may be of different section to provide a shock absorbing portion of varying width around the container. Thus, if the container is substantially rectangular or square the foot may be circular in configuration and vice versa.

Such packaging avoids the above difficulties of the prior art. To use the package an appropriate quantity of water is measured out into a vessel such as a sprayer tank and then the envelope, e.g. a bag or sachet, is removed, e.g. tipped, from the container and placed whole into the vessel with a predetermined measure of water and mixed. The contents of the envelope are released when, for example, the material from which e.g a bag or sachet is made dissolves or disperses throughout the water together with the chemical. Thus, there is no possibility of spilling the chemical liquid since it is still in the form of a closed and sealed package when it is mixed with the large volume of water. During mixing any splashing that occurs is splashing only of a diluted chemical and this is naturally not so toxic to personnel or so damaging to the environment should any splashing or spillage occur.

The chemicals which may be packaged include those which are potentially toxic or damaging or detrimental to health or to the environment. They include pesticides for example fungicides, insecticides or herbicides (for example hydroxybenzonitrile herbicides, e.g. bromoxynil or ioxynil or derivatives thereof such as the salts or esters, e.g. heptanoates or octanoates) and, more generally, chemicals which are to be dissolved or dispersed in a large volume of water or aqueous liquid, such as compounds, e.g. metronidazole, used to combat spoilage in industrial aqueous liquids, or compounds for addition to the aqueous circuits of e.g. domestic or industrial heating systems, compounds for addition to swimming pools, photographic materials, inks, dyestuffs, non-aqueous organic acids and cement additives. The pesticides include, e.g. molluscicides for addition to, for example, ponds or streams. When the envelope material is a PVA borates, chlorides and chlorates should generally not be present in the packaged liquid in amounts effective to lead to deterioration of the envelope material or that material should be protected from them.

Suitable water soluble or dispersible materials which are insoluble in the organic solvents used to dissolve or disperse the chemical include polyethylene oxide or methyl cellulose, but preferably the envelope, e.g. a bag or sachet, comprises or is made from polyvinyl alcohol film, i.e. partially or fully alcoholysed or hydrolysed e.g. 40–99%, preferably 70–92% alcoholysed or hydrolysed, polyvinyl acetate film.

The polyvinyl alcohol film may be unoriented, mono-axially oriented or bi-axially oriented. Water soluble materials are preferred. The materials used will generally be cold water soluble; cold water soluble PVA is preferred. It will be understood that other materials may be used when the packaged liquid is to be dissolved or dispersed in warm or hot water.

The maximum tensile strength of the material of the envelope is preferably at least 20, more preferably from 30 to 80N/mm and the elongation at break is preferably 200 to 380%, more preferably from 220 to 350%. Testing for these values is generally carried out at 23° C. and 50% relative humidity. The thickness of the envelope material is preferably from 10 to 500, more preferably 20 to 100 micrometers. Combinations of these physical properties are especially preferred.

The polyvinyl alcohol material may be extruded as a tube and then inflated to bi-axially orient it or, more preferably, it may be cast. When a cast film is used as is preferable, a tube is formed from the film and the edges heat sealed along the length of the tube. The tube is sealed at one end and then filled with the desired quantity of the chemical. The tube is again sealed above the quantity of chemical to close the envelope and form, for example, a closed bag or sachet. An air space is preferably left above the liquid in the closed envelope and, in addition, the combined volume of the air space and liquid is preferably less than the maximum possible capacity of the envelope so that it is loosely filled and can flex.

When heat seals are made in order to form or close the envelope containing liquid in the package according to the invention the sealing temperature is generally from 140° to 220° C., preferably 160° to 180° C. The jaw pressure is generally from 1 to 3½ kg/cm², preferably 1½ to 2½ kg/cm². The dwell time is generally 200 msec to 1.5 sec, preferably 450 msec to 1 sec.

In order to ensure optimum processability the heat sealing is generally carried out at 15° to 25° C. and 15 to 85% relative humidity (RH). The relative humidity is preferably 35 to 55%. Some routine experimentation may be required to obtain suitable heat seals depending on the envelope material, e.g. the particular grade and the thickness of PVA chosen. The quality of the seals can be checked by visual inspection for areas of opacity or for bubbles or, for example, by inflation of bags without liquid contents. Imperfections in the seal may give rise to a lack of water solubility or water dispersibility of the seal. The heat sealing process can be carried out on conventional heat sealing equipment which permits control and variation of the sealing jaw temperature, jaw pressure and dwell time.

In practice the envelopes according to the invention should release their contents in less than about 10 minutes. When a phytosanitary chemical is packaged the packaged chemical will be placed in the spray tank of a conventional sprayer. The tank will generally be partly filled with water, and the packaged chemical added. When the tank is provided with means to agitate the water the contents of the bag will be released more rapidly. It is preferred that release should take place in less than about a minute, for example in 30 to 40 seconds. It will be understood that the time taken to release the chemical will depend on a number of factors apart from the nature of the bag, including the temperature of the water and the level of agitation.

When the envelope is a bag or sachet the thickness of the walls should be kept to a minimum, provided that the walls have adequate strength in order to facilitate rapid dissolution or dispersion in water. A thickness of e.g. about 30 microns is particularly suitable, although large sachets may require thicker walls. The thicker the wall, the longer dissolution or dispersion of the wall material will take. It will be understood that the envelope according to the invention may comprise an area of wall which is more readily dissolved or dispersed than the rest to facilitate more rapid release of the contents of the envelope.

Suitable organic liquid solvents include petroleum based solvents, e.g. petroleum ethers, mineral oils, aliphatic or aromatic hydrocarbons, e.g. hexane, octane, cyclohexane, benzene, xylene and naphthalene, halogenated aliphatic or aromatic hydrocarbons, e.g. carbon tetrachloride, chloroform, methylene chloride and chlorobenzene, esters e.g. amyl acetate, ketones, e.g. cyclohexane, ethers, or a higher alcohol (lower alcohols may migrate through the water soluble or water dispersible materials described above: this can result in product appearing on the outside of the envelope). It will be understood that mixtures of solvents, e.g. mixtures of a hydrocarbon solvent with another solvent, e.g. a ketone or a higher alcohol, may also be used. The organic liquid must be reasonably dry and typically contains less than 2 to 3% of water to ensure that it does not leak prematurely from the envelope.

The liquid contents of the envelope may be thickened or rendered thixotropic. An increased viscosity in the contents can reduce the likelihood of the envelope being ruptured if the package is subjected to mechanical shock, particularly as the envelope comprises a flexible wall. The contents of the envelope may be rendered more viscous or thixotropic by the inclusion of additives, for example, a modified organophilic, or bentonite, lecithin, polymethylene oxide or silica gel.

The concentrations of pesticide or herbicide dissolved or dispersed in the organic liquid will generally be those conventionally used: in order to reduce the bulk of each envelope, however, concentrations may be increased. Each envelope will preferably contain at least about 500 ml and will preferably contain a convenient standard volume, for example 500 ml or 1 liter, although it will be appreciated that any convenient standard volume may be chosen. The envelope will generally contain from a quarter liter to 3 liters of liquid.

Preferably the outside of the container is printed with information concerning the contents of the envelope, instructions for use, and any warnings concerning the nature and toxicity of the chemical. This information may be carried on the foil lid or on a label attached to the side wall of the outer container.

The space between the envelope and the outer container (which is preferably at least about 5% of the volume of the container; the space will preferably not be more than about 30%: larger spaces could be used but may be less attractive commercially: about 25% is especially preferred. The space is preferably isolated from the atmosphere for example by a hermetic seal on the outer container. The relative humidity in the space is preferably from 45 to 65% (about 50% being most preferred) at a temperature of 20° C. When the envelope material is PVA film the mechanical properties of the film are affected by its moisture content: moisture in the film is in equilibrium with moisture both in any air space inside the envelope and in any space between the envelope and the outer container. The point of equilibrium changes with temperature so that the film may either absorb moisture or release it during storage. A relative humidity of 45 to 65% at 20° C. has been found to preserve optimum storage properties of the envelope material.

The packaging in accordance with the preferred aspects of this invention provides a tough, two stage packaging which provides for the safe transport of concentrated chemicals and allows handling of potentially toxic chemicals with the minimum risk to personnel and the environment.

The following Example illustrates the production of a water soluble package according to the invention:

EXAMPLE

PVA film was used to form bags containing a liquid herbicide by the following procedure using conventional bag-mating equipment.

The PVA film used was SYNTANA Type KA cold water soluble PVA film, thickness 40 micrometers, with a degree of saponification of 88 mol %.

The liquid herbicide was a mixture of bromoxynil and ioxynil esters in solution in a naphthalene solvent. The liquid contained less than 3% water.

An open-topped bag was produced from the PVA film by forming the film around a shoulder and then heat sealing simultaneously the bottom and side of the bag. A jaw pressure of 2 kg/cm$^2$ was used, with a jaw temperature of 160° C. and a dwell time of 1 second. The ambient temperature was 18° C. and the relative humidity 35%.

500 ml of liquid herbicide was then dispensed into the bag the top of which was then sealed leaving an air space of 4 to 5% volume within the bag. Each bag was 120 mm by 205 mm and 10 bags per minute were produced.

Each filled bag was heat sealed at the top after dispensing of the liquid leaving an air space of 4 to 5% of the bag volume, the bag being about 80% full of liquid. The bag is therefore both incompletely filled and has an air space above the liquid.

Each bag was then placed into a container as illustrated in the accompanying drawings. The container material was polypropylene. Each container was sealed using a laminated top comprising PET (polyethylene terephthalate), aluminium and paper layers. The PET layer was heat sealed to the top flange of the container leaving an air space between the bag and the container. The relative humidity in the air space was 50% at 20° C.

A further example of a package in accordance with this invention will now be described by reference to the accompanying drawings, in which.

Figure 1:
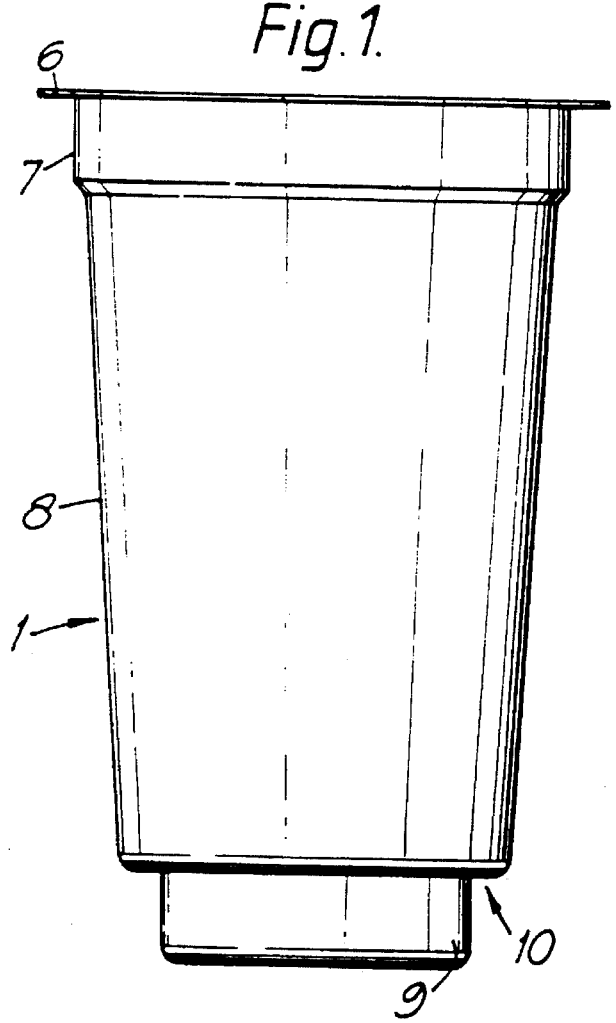
FIG. 1 is a side elevation of the complete package.

The package comprises an outer container 1 having a foil lid 2 surrounding and enclosing an envelope (a bag or sachet) 3. The bag or sachet 3 is made of cold water soluble grade polyvinyl alcohol film 4 made from 88% alcoholysed polyvinyl acetate having a wall thickness of 30 microns which is heat-sealed into the form of a sachet containing 500 milliliters of a concentrated dispersion 5 of a chemical in an organic liquid. The sachet 3 is housed inside the container 1 which includes a substantially flat top flange 6 connected by upper collar portion 7 to a tapering side wall 8. The container 1 also includes a foot 9 which is joined to the lowest end of the side wall 8 by a shock absorbing section 10. The container has an approximately rectangular cross-section with rounded corners between adjacent sides and with outwardly bowed faces as shown most clearly in FIG. 2. The rectangular shape of the container allows relatively efficient packing together of a number of containers. The container is also tapered downwardly as shown in FIG. 1, in this case by 3 to 4° from vertical, and this allows a number of containers to be nested together when empty for easy storage or disposal. The taper also means that the sachet is supported by the walls of the container against downward movement. The container 1 is injection moulded from a block polymer polypropylene having a high melt flow index and typically having a constant wall thickness throughout of, for example, substantially one millimeter. The container is made to be translucent so that, as described below, leakage of the sachet can be detected without opening the container. In an alternative embodiment the foot only can be made translucent so that leakage can be seen. Further, polypropylene is water repellent and this makes washing of the container easier. The material from which the container is made, in this embodiment polypropylene, is sufficiently rigid to support and protect the sachet but also has a degree of flexibility which helps absorb shocks or blows to the package.

Figure 3:
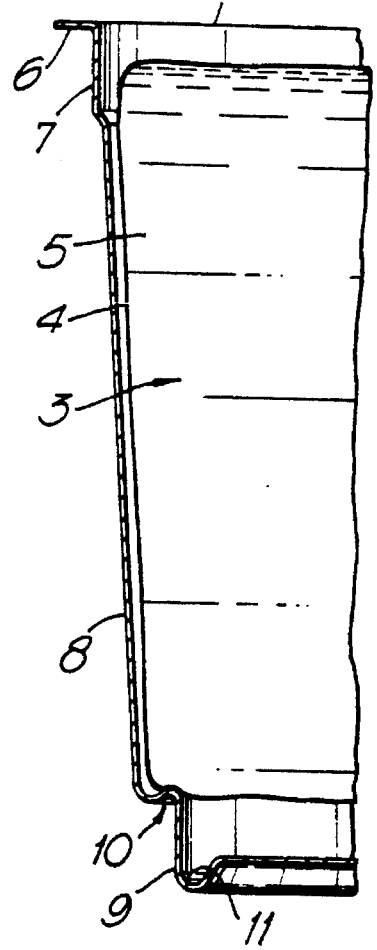
FIG. 3 shows half of a longitudinal radial section through the complete package.

The shock absorbing section 10 is corrugated being S-shaped in cross-section as shown in FIG. 3 the ratio of the length of the section to its thickness being about 9:1, this ratio being chosen to allow the desired amount of flexing having regard to the flexibility of the material from which it is formed.

The corrugated section forms generally transverse connection joining the lower edge of the side wall 8 to the upper edge of the foot 9 which is capable of flexing as a result of the natural resilience of the thermo-plastics material to allow some relative upwards and downwards movement to occur between the foot 9 and the side wall 8. This flexing adsorbs shock loads applied to the container 1 for instance if it is inadvertently dropped, e.g. during transport or handling.

During transport of the packages any outer packaging containing an array of such packages may be dropped or at least suffer substantial shock loads as it is transported by, for example, lorry, or even when it is lifted and lowered by, for example, a fork lift truck. The shock absorbing portion formed between the foot and the side wall of the container flexes and absorbs such shock loads and this partly cushions the loads applied to the envelope and ensures that the outer container does not split under the application of such a shock load. Equally, after the package has been removed from any outer container the shock absorber absorbs loads if the package is, inadvertently, dropped onto a solid floor just before it is opened to gain access to the envelope. Typically, if the package falls on its foot the shock absorbing section absorbs any shock load so imposed on the container. Equally, if the container falls on its side wall the rounded nature of the side wall means that the side wall can flex and again absorb any shock loads. Further, if the container lands upon its top flange this tends also to flex to absorb the shock load.

Figure 2:
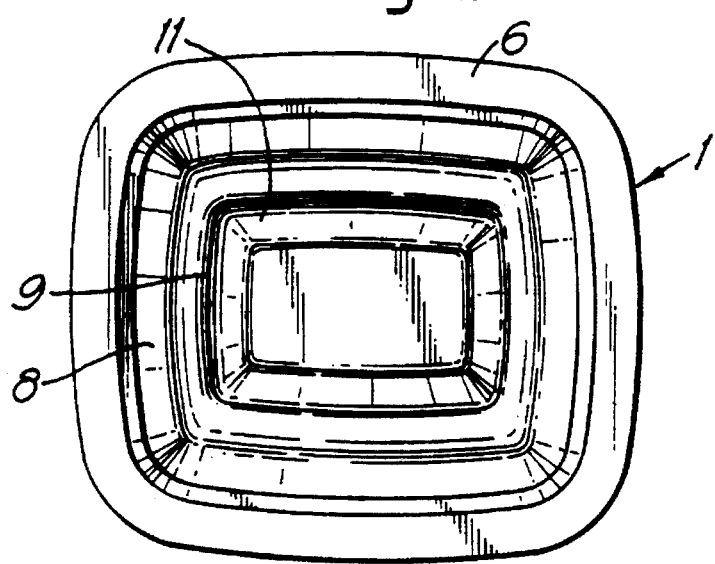
FIG. 2 is an underneath view of the outer container.

As can be seen from FIG. 2 the foot 9 is formed with a raised central section surrounded by trough 11. The trough is provided to collect any liquid which accidently leaks from the sachet before use. As the container, or at least this part of it, is translucent it is possible for the user to look at the foot and see whether the sachet has leaked before opening the container. Thus accidental contact with leaked contents can be avoided. As will be appreciated from FIG. 2 the raised control portion of the foot leaves a space underneath it which, when the container is stood on a shelf, would form a closed cavity. This could cause problems because if the sachet does leak into the container then vapour from the concentrate could pass through the container material into the cavity where it would be trapped and could attack the shelf or any coating on the shelf. Thus, to allow ventilation of this cavity the underside of the trough 11 is formed with at least one recess or groove (not shown) directed radially of the foot.

In this embodiment the corrugated section 10 also provides an internal annular shoulder to the container upon which the sachet rests. The curve of the corrugation provides a smooth surface which will not strain or puncture the sachet. The sachet is thus supported above the bottom of the container resulting in further isolation from mechanical shock. The sachet can also flex under stress into the space to absorb shock.

The interior of the container is deliberately made to be smooth so as to allow the sachet to slide easily out of the container for use.

The sachet 3 is held inside the container 1 by the foil lid 2 which is heat-sealed onto the flange 6 of the container 1 or which may alternatively be connected by an adhesive.

The foil lid 2 in this embodiment is made from a heat sealable laminated material such as a polyethylene terephthalate/aluminium/paper laminate and is larger than the external diameter of the flange 6 to leave a large flap around the container which can be used to tear-off the lid.

The outer container 1 and lid 2 provide protection for the sachet 3 and so protect it from contact with water and hence its premature dissolution. It also provides an additional barrier layer around the concentrate 5 inside the bag or sachet 3 to provide an additional Partier in case of rupture of the bag or sachet 3 which prevents the potentially harmful chemical 5 from contact with personnel or the environment. However, to use the concentrate, the foil lid 2 is simply removed and then the sachet, still sealed, is dropped into a sprayer tank containing a predetermined amount of water. The material 4 of the bag or sachet dissolves rapidly in the water so allowing the contents 5 to be dispersed throughout the water in the sprayer tank on mixing. The outer container 1 is not contaminated with the concentrated chemical and can thus be disposed of without taking any special precautions and the personnel dealing with the concentrated chemical never come into contact with it, so reducing the hazards and risks involved in handling such potentially harmful materials.

We claim:

1. A package for a liquid comprising an outer container and a sealed water-soluble or water-dispersible envelope within the outer container, said sealed envelope containing the liquid, the liquid in the sealed envelope being potentially toxic or damaging or detrimental to health or to the environment, the outer container comprising a body-part portion surrounding the sealed envelope and a base-part including a shock-absorbing base, the outer container further comprising means for supporting the sealed envelope, said means being within the base-part portion on a side wall of the outer container and supporting the sealed envelope above a bottom of the outer container such that a space completely separates the sealed envelope from a bottom of the outer container.

2. A package according to claim 1, wherein the sealed envelope is disposed in the outer container in a manner such that there is a space between the sealed envelope and the side wall of the outer container.

3. A package according to claim 2, wherein the space between the sealed envelope and the outer container side wall has a volume less than 30% of the volume of the outer container.

4. A package according to claim 1, wherein the base-part comprises the shock-absorbing base joined to the body-portion by a flexible strip.

5. A package according to claim 4, wherein the flexible strip comprises a corrugation in the side wall of the outer container extending generally inwardly of the outer container from a bottom of the body-part portion to the shock-absorbing base.

6. A package according to claim 5, wherein the flexible strip is formed by a sinuous formation in the side wall of the outer container spaced from the bottom of the outer container, and wherein the means to support the sealed envelope comprises the sinuous formation which forms an internal shoulder of the outer container on which the sealed envelope is supported.

7. A package according to claim 1, wherein the outer container is substantially rigid.

8. A package according to claim 1, wherein an inside surface of the outer container is configured and adapted to facilitate sliding exit of the sealed envelope from the outer container.

9. A package according to claim 1, in which the outer container comprises polypropylene.

10. A package according to claim 1, in which the outer container is translucent or includes a translucent region.

11. A package according to claim 1, wherein the base-part includes a recessed portion inside the container to collect any liquid which may escape from the envelope.

12. A package according to claim 11, wherein said recessed portion is formed between an outer side wall of the shock-absorbing base and a raised central portion of the base-part.

13. A package according to claim 12, wherein the underside of the recessed portion forms an annular stand for the sealed envelope and at least one slot or groove is provided in said underside to enable communication between a region under said raised central portion of the base-part and the exterior when the package is stood on a surface.

14. A package according to claim 1, in which the side wall of the outer container tapers towards the base part allowing the outer container, when empty, to nest in other similar shaped empty outer containers.

15. A package according to claim 1, wherein the potentially toxic or damaging liquid is or comprises a phytosanitary chemical.

16. A package according to claim 1, wherein the potentially toxic or damaging liquid is or comprises a pesticide.

17. A package according to claim 1, wherein the potentially toxic or damaging liquid comprises one of a fungicide, an insecticide and a herbicide.

18. A package according to claim 1, wherein the sealed envelope contains a liquid with increased viscosity.

19. A package according to claim 1, wherein a combined volume of air space and liquid in the sealed envelope is less than a maximum possible capacity of the sealed envelope.

20. A package according to claim 1, wherein the outer container is semi-rigid or flexible.

21. A package according to claim 1, wherein the outer container has a degree of flexibility to help absorption of shock and blows to the package.

22. A package according to claim 1, wherein the liquid is one of-a concentrated solution, a dispersion, an emulsion or a suspension.

23. A package according to claim 1, in which the outer container side wall tapers towards the base part to allow support against downward movement of the sealed envelope.

24. A package according to claim 1, in which the outer container has a substantially square or rectangular cross section.

25. A package according to claim 1, in which the outer container has a substantially square or rectangular cross section with round corners or sides.

26. A package according to claim 1, wherein a combined volume of air space and liquid in the sealed envelope is less than a maximum possible capacity of the sealed envelope.

27. A package according to claim 1, wherein the outer container is flexible.

28. A package according to claim 27, wherein the outer container has a degree of flexibility to help absorption of shock and blows to the package.

29. A package according to claim 27, wherein the liquid is one of a concentrated solution, dispersion, emulsion and suspension.

30. A package according to claim 27, in which the outer container side wall tapers towards the base part to allow support against downward movement of the sealed envelope.

31. A package according to claim 27, in which the outer container has a substantially square of rectangular cross section.

32. A package according to claim 27, in which the outer container has a substantially square or rectangular cross section with round corners or sides.

* * * * *